US009358258B2

(12) United States Patent
Kim et al.

(10) Patent No.: US 9,358,258 B2

(45) Date of Patent: Jun. 7, 2016

(54) **ISOLATED BACTERIOPHAGE HAVING *E. COLI*-SPECIFIC BACTERICIDAL ACTIVITY AND ANTIBACTERIAL COMPOSITION COMPRISING THE SAME**

(71) Applicant: CJ CHEILJEDANG CORPORATION, Seoul (KR)

(72) Inventors: Jae Won Kim, Seoul (KR); Young Wook Cho, Seoul (KR); Eun Mi Shin, Incheon (KR); Young Sa Kim, Seoul (KR); Si Yong Yang, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/345,189

(22) PCT Filed: Nov. 14, 2012

(86) PCT No.: PCT/KR2012/009613
§ 371 (c)(1),
(2) Date: Mar. 14, 2014

(87) PCT Pub. No.: WO2013/073843
PCT Pub. Date: May 23, 2013

(65) Prior Publication Data

US 2014/0356330 A1 Dec. 4, 2014

(30) Foreign Application Priority Data

Nov. 14, 2011 (KR) ........................ 10-2011-0118446

(51) Int. Cl.

| | |
|---|---|
| ***A61K 35/76*** | (2015.01) |
| ***C12N 7/00*** | (2006.01) |
| ***A23K 1/16*** | (2006.01) |
| ***A23K 1/18*** | (2006.01) |

(52) U.S. Cl.
CPC ............... *A61K 35/76* (2013.01); *A23K 1/1631* (2013.01); *A23K 1/184* (2013.01); *A23K 1/1893* (2013.01); *C12N 7/00* (2013.01); *A23V 2200/32* (2013.01); *C12N 2795/00021* (2013.01); *C12N 2795/00032* (2013.01)

(58) Field of Classification Search
None
See application file for complete search history.

(56) References Cited

U.S. PATENT DOCUMENTS

| | | | |
|---|---|---|---|
| 6,485,902 | B2 | 11/2002 | Waddell et al. |
| 6,942,858 | B1 | 9/2005 | Ghanbari et al. |
| 2002/0090356 | A1 | 7/2002 | Waddell et al. |

FOREIGN PATENT DOCUMENTS

| | | | |
|---|---|---|---|
| CN | 101724607 | A | 6/2010 |

OTHER PUBLICATIONS

Ackerman, "Frequency of morphological phage descriptions in the year 2000," *Archives of Virology* 146:843-857 (2001).

Denou et al., "T4 phages against *Escherichia coli* diarrhea: Potential and problems," *Virology* 388:21-30 (2009).

Jamalludeen et al., "Isolation and characterization of nine bacteriophages that lyse O149 enterotoxigenic *Escherichia coli*," *Veterinary Microbiology* 124:47-57 (2007).

Mason et al., "Transgenic plants as vaccine production systems," *Trends in Biotech* 13:388-392 (1995).

Nagy et al., "Immunization of Suckling Pigs Against Enteric Enterotoxigenic *Escherichia coli* Infection by Vaccinating Dams with Purified Pili," *Infection and Immunity* 21(1):269-274 (Jul. 1978).

Nagy et al., "Enterotoxigenic *Escherichia coli* (ETEC) in farm animals," *Vet. Res.* 30:259-284 (1999).

Schmidt et al., "Transduction of Enteric *Escherichia coli* Isolates with a Derivative of Shiga Toxin 2-Encoding Bacteriophage phi3538 Isolated from *Escherichia coli* O157:H7," *Applied and Environmental Microbiology* 65(9):3855-3861 (Sep. 1999).

Smith et al., "The Control of Experimental *Escherichia coli* Diarrhoea in Calves by Means of Bacteriophages," *Journal of General Microbiology* 133:111-1126 (1987).

Chinese Office Action (translation) for counterpart Chinese Patent Application No. 201280055906.2 dated Nov. 26, 2014.

*Primary Examiner* — Nicole Kinsey White
(74) *Attorney, Agent, or Firm* — Seed IP Law Group PLLC

(57) ABSTRACT

The present invention relates to a novel bacteriophage having an *E. coli*-specific bactericidal activity, a composition for the prevention or treatment of infectious diseases caused by Enterotoxigenic *E. coli* comprising the bacteriophage as an active ingredient, an antibiotic comprising the bacteriophage as an active ingredient, a feed additive composition comprising the bacteriophage as an active ingredient, a sanitizer or cleaner comprising the bacteriophage as an active ingredient, and a method for treating colibacillosis using the bacteriophage. The novel bacteriophage of the present invention has a specific bactericidal activity against pathogenic *E. coli*, and excellent acid- and heat-resistance. Therefore, the novel bacteriophage can be used for the prevention or treatment of swine colibacillosis, which is an infectious disease caused by pathogenic *E. coli*, and can also be widely used in animal feed additive compositions, sanitizers, and cleaners.

5 Claims, 4 Drawing Sheets

ISOLATED BACTERIOPHAGE HAVING *E. COLI*-SPECIFIC BACTERICIDAL ACTIVITY AND ANTIBACTERIAL COMPOSITION COMPRISING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_418USPC_SEQUENCE_LISTING.txt. The text file is 10.7 KB, was created on Mar. 9, 2014, and is being submitted electronically via EFS-Web.

TECHNICAL FIELD

The present invention relates to a novel isolated bacteriophage showing an *E. coli*-specific bactericidal activity, and an antibacterial composition comprising the same.

BACKGROUND ART

*E. coli* is a Gram-negative, short rod-shaped bacterium belonging to the genus *Escherichia* and the family Enterobacteriaceae, and is found as part of the normal flora in the intestines of various animals including mammals. It was revealed that most strains of *E. coli* are non-pathogenic and can cause opportunistic infections, but some highly pathogenic strains cause diverse intestinal diseases and sepsis in mammals including humans. Of them, strains causing gastrointestinal diseases can be largely classified into six groups based on their virulence, Enterotoxigenic *E. coli* (ETEC), Enteropathogenic *E. coli* (EPEC), Enterohemorrhagic *E. coli* (EHEC), Enteroaggregative *E. coli* (EAEC), Enteroinvasive *E. coli* (EIEC), and Necrotoxigenic *E. coli* (NTEC). Enterotoxigenic *E. coli* (ETEC) is known to be associated with infections in pigs. In general, diseases caused by bacterial or viral infections can be diagnosed by identification of the pathogens. However, since *E. coli* is present in the intestines of healthy animals, early diagnosis of diseases caused by *E. coli* infections is difficult (Korean Patent No. 963157).

ETEC is a Gram-negative rod-shaped bacterium, and either motile with peritrichous flagella or non-motile without flagella. ETEC is an aerobic or facultative anaerobic bacterium producing acid and gas from lactose and fructose, and grows well on common media at a temperature between 7-48° C., temperature being optimal at 35-37° C., and at pH 4.5-9.0. ETEC produces a toxin similar to the cholera toxin, and this toxin can be divided into a heat-labile enterotoxin (LT) losing its activity when heated at 60° C. for 10 minutes and a heat-stable enterotoxin showing a resistance after heated at 100° C. for 30 minutes. When infected, cholera-like symptoms are shown, and it proliferates in the upper part of the small intestine and the bacterial concentration reaches $10^7$-$10^8$ cfu (colony formation unit) per ml, leading to occurrence of *E. coli* infectious diseases.

Recently, in light of the trend toward large-scale corporate swine production, colibacillosis in pigs has become a common and frequent emerging problem in piggeries (Park Young-il, Sun-Jin Publishing Co. 353-359, 1998). In Korea, the recent increasing occurrence of swine colibacillosis has been causing growth retardation and death of young pigs due to diarrhea, resulting in tremendous economic losses to farmers (Hong Eu-Chul, master's thesis, Dankook University, Addition Effect of Egg Yolk in Early Weaned Piglets, 2001).

Many antibiotics have been used for the prevention and treatment of swine colibacillosis, but the misuse and overuse of antibiotics have given rise to the serious problems of drug resistance and drug residues in pigs. Thus, the use of antibiotics has been restricted in many countries worldwide (Mason H S et al., Trends in Biotech. 13:388-392, 1995).

Meanwhile, bacteriophage is a specialized type of virus that infects only particular bacteria and controls the growth of bacteria, and can self-replicate only inside host bacteria. Bacteriophage consists of genetic material in the form of single or double stranded DNA or RNA. Based on their morphology, bacteriophages are divided into Myoviridae, Siphoviridae, and Podoviridae, which are characterized by contractile, long non-contractile, and short tails, respectively (Arch Virol (2001) 146:843-857; Elizabeth Kutter et al., Bacteriophages Biology and Application; CRC press).

After the discovery of bacteriophages, a great deal of effort was initially placed in using them for infectious-disease therapy. However, compared to antibiotics having broad target spectrum, bacteriophages were seen as unnecessary due to having a specific target spectrum. Nevertheless, the misuse and overuse of antibiotics resulted in rising concerns about antibiotic resistant bacteria and harmful effects of residual antibiotics in foods (Cislo, M et al. Arch Immunol. Ther. Exp. 1987.2:175-183; Kim sunghun et al., bacteriophage, New Alternative Antibiotics. BRIC).

These growing concerns have led to a resurgence of interest in bacteriophage. Seven bacteriophages for control of *E. coli* 0157:H are disclosed in U.S. Pat. No. 6,485,902 (2002) and two bacteriophages for control of various microorganisms are disclosed in U.S. Pat. No. 6,942,858 (issued to Nymox in 2005).

DISCLOSURE OF INVENTION

Technical Problem

In order to overcome problems occurring upon the misuse or overuse of broad spectrum antibiotics, such as antibiotics resistant bacteria and antibiotic residues in foods, the present inventors isolated a novel bacteriophage from natural sources, in which the bacteriophage has a specific bactericidal activity against *E. coli* causing major diseases in livestock. It was found that the bacteriophage has a specific bactericidal activity against pathogenic *E. coli*, in addition to excellent acid- and heat-resistance, as identified by the morphological, biochemical and genetic properties thereof. It was also found that the bacteriophage can be applied to compositions for the prevention or treatment of infectious diseases in livestock caused by pathogenic *E. coli*, and to various products for the effective prevention and control of pathogenic *E. coli* proliferation, including livestock feed additives, drinking water for livestock, barn sanitizers, and cleaners for meat products.

Solution to Problem

An object of the present invention is to provide a novel bacteriophage having a specific bactericidal activity against Enterotoxigenic *E. coli.*

Another object of the present invention is to provide a composition for the prevention or treatment of infectious diseases caused by Enterotoxigenic *E. coli*, comprising the bacteriophage as an active ingredient.

Still another object of the present invention is to provide an antibiotic, comprising the bacteriophage as an active ingredient.

Still another object of the present invention is to provide a feed additive composition, comprising the bacteriophage as an active ingredient.

Still another object of the present invention is to provide a sanitizer or cleaner, comprising the bacteriophage as an active ingredient.

Still another object of the present invention is to provide a method for treating colibacillosis using the bacteriophage or the composition.

Advantageous Effects of Invention

The novel bacteriophage of the present invention has a specific bactericidal activity against Enterotoxigenic *E. coli*, and excellent acid- and heat-resistance. Therefore, the novel bacteriophage can be used for the prevention or treatment of swine colibacillosis, an infectious disease caused by pathogenic *E. coli*, and can also be widely used in animal feed additive compositions, sanitizers, and cleaners.

BEST MODE FOR CARRYING OUT THE INVENTION

In one aspect to achieve the above objects, the present invention provides a novel bacteriophage having a specific bactericidal activity against Enterotoxigenic *E. coli* (ETEC).

Figure 3:
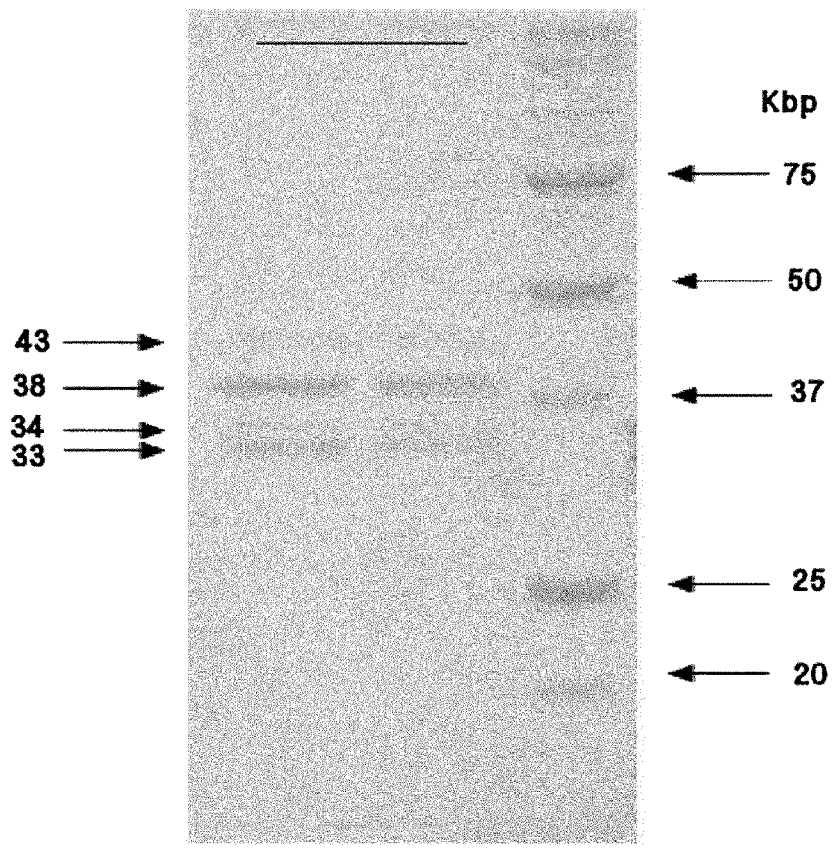
FIG. 3 is the result of SDS-PAGE of the isolated bacteriophage ΦCJ13.

The present inventors collected fecal samples from Samhwa GPS Breeding Agri., Inc. in the Kwangcheon area, Hong sung-gun, Chung Cheong Province, and isolated therefrom bacteriophages that can selectively infect and lyse the host cell ETEC. A morphological examination under an electron microscope confirmed that the bacteriophage has a specific bactericidal activity against Enterotoxigenic *Escherichia coli*; belongs to Podoviridae having morphological features consisting of an isometric capsid and no tail (FIG. 1); has a total genome size of approximately 35 kbp; and comprises major structural proteins of approximately 43 kDa, 38 kDa, 34 kDa, and 33 kDa as measured by a protein pattern analysis (FIG. 3). In addition, the bacteriophage of the present invention has a species specificity of selectively infecting ETEC among *E. coli* (Table 1).

Furthermore, the results of analyzing its genetic features showed that the bacteriophage includes nucleic acid molecules represented by SEQ ID NOs: 1 to 6 within the total genome. Based on SEQ ID NOs: 1 to 6, genetic similarity with other species was compared. It was found that various similarities of 86%-100% were observed depending on the each nucleic acid fragments, but there were no bacteriophages showing 100% similarity on the all of the fragments, indicating that the bacteriophage is a novel bacteriophage (Table 2). Based on more detail analysis of genetic features, it was found that PCRs using the bacteriophage-specific primer sets, namely, SEQ ID NOs: 7 and 8, SEQ ID NOs: 9 and 10, SEQ ID NOs: 11 and 12, SEQ ID NOs: 13 and 14, SEQ ID NOs: 15 and 16, and SEQ ID NOs: 17 and 18 produce products of specific sizes.

Figure 5:
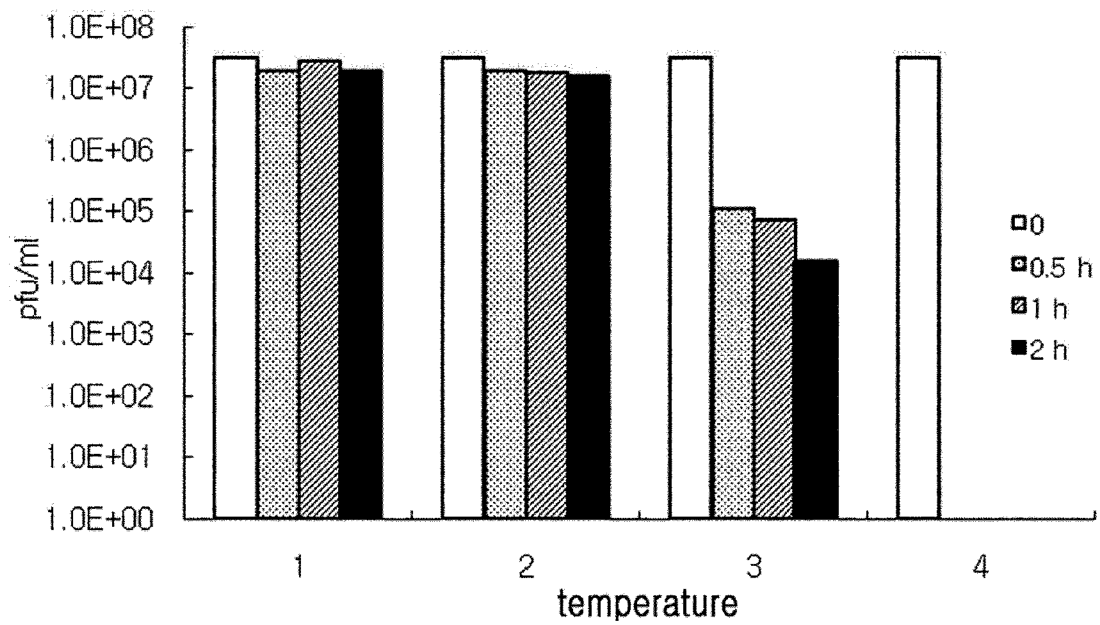
FIG. 5 is the result of a heat-resistance assay on the bacteriophage ΦCJ13.

Meanwhile, when ETEC was infected with the bacteriophage, the phage plaques (clear zone on soft agar created by host cell lysis by one bacteriophage) were observed and had the same size and turbidity, indicating that the bacteriophage inhibited growth of ETEC by lysis of ETEC. By examination of the stability of the bacteriophage under various temperature and pH conditions, it was found that the bacteriophage is stable in a wide range of pH environments from pH 3 to pH 10 and temperature environments from 40° C. to 60° C., and in particular, it has heat-resistance at high temperature (FIG. 5). Such properties of ETEC-specific bactericidal activity, and acid- and heat-resistance allow application of the bacteriophage of the present invention under various temperature and pH conditions upon the production of prophylactic or therapeutic compositions for ETEC-mediated diseases in pigs and various products including the bacteriophage as an active ingredient.

Accordingly, the present inventors designated the bacteriophage having a specific bactericidal activity against ETEC and the above characteristics as "Bacteriophage ΦCJ13", and deposited it at the Korean Culture Center of Microorganisms (361-221, Honje 1, Seodaemun, Seoul) on Nov. 7, 2011 under accession number KCCM11217P.

In another aspect to achieve the above objects, the present invention provides a composition for the prevention or treatment of infectious disease caused by Enterotoxigenic *E. coli* (ETEC), comprising the bacteriophage as an active ingredient.

Having a specific bactericidal activity against ETEC, the bacteriophage of the present invention may be used for the purpose of preventing or treating the diseases caused by ETEC. Preferably, an example thereof includes swine colibacillosis caused by ETEC, but is not limited thereto.

As used herein, the term "colibacillosis" means a disease caused by infection of livestock with pathogenic *E. coli*, and shows symptoms such as sepsis, diarrhea (neonatal diarrhea and post-weaning diarrhea), and toxemia (edema and cerebrospinal angiopathy). Of them, sepsis is an acute systemic infection that frequently occurs in 2-3 day-old-neonatal pigs, and has a high mortality rate. Diarrhea is the most common outcome of gastrointestinal tract infections that occur during the lactation period within 1-2 weeks after birth and immediately after the weaning period, and causes death or growth retardation. Toxemia occurs in 8-12 week-old piglets after the weaning period, and is accompanied by edema and neurologic signs, followed by sudden death As used herein, the term "prevention" means all of the actions in which disease progress is restrained or retarded by the administration of the bacteriophage or the composition, and the term "treatment" means all of the actions in which the condition has taken a turn for the better or been restrained or modified favorably by the administration of the bacteriophage or the composition.

The composition of the present invention includes ΦCJ13 in an amount of $5\times10^{2}$ to $5\times10^{12}$ pfu/ml, and preferably in an amount of $1\times10^{6}$ to $1\times10^{10}$ pfu/ml.

On the other hand, the composition of the present invention may further include a pharmaceutically acceptable carrier.

As used herein, the term "pharmaceutically acceptable carrier" refers to a carrier or diluent that does not cause significant irritation to an organism and does not abrogate the biological activity and properties of the administered compound. For formulation of the composition into a liquid preparation, saline, sterile water, Ringer's solution, buffered physiological saline, albumin infusion solution, dextrose solution, maltodextrin solution, glycerol, ethanol, and mixtures of one or more thereof may be used for a pharmaceutically acceptable carrier which is sterile and biocompatible. If necessary, other conventional additives such as antioxidants, buffers, and bacteriostatic agents may be added. Further, diluents, dispersants, surfactants, binders and lubricants may be additionally added to the composition to prepare injectable formulations such as aqueous solutions, suspensions, and emulsions, or oral formulations such as pills, capsules, granules, or tablets.

The prophylactic or therapeutic compositions of the present invention may be applied or sprayed to the afflicted area, or administered by oral or parenteral routes. The parenteral administration may include intravenous, intraperitoneal, intramuscular, subcutaneous or topical administration. The dosage suitable for applying, spraying, or administrating the composition of the present invention will depend upon a variety of factors including formulation method, the mode of administration, the age, weight, sex, condition, and diet of the patient or animal being treated, the time of administration, the route of administration, the rate of excretion, and reaction sensitivity. A physician or veterinarian having ordinary skill in the art can readily determine and prescribe the effective amount of the composition required.

Examples of the oral dosage forms including the composition of the present invention as an active ingredient include tablets, troches, lozenges, aqueous or emulsive suspensions, powder or granules, emulsions, hard or soft capsules, syrups, or elixirs. For formulation such as tablets and capsules, a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax may be used. For capsules, a liquid carrier such as lipid may be further used in addition to the above-mentioned compounds.

The parenteral dosage forms including the composition of the present invention as an active ingredient may be formulated into injections via subcutaneous, intravenous, or intramuscular routes, suppositories, or sprays inhalable via the respiratory tract, such as aerosols. Injection forms may be prepared by dissolving or suspending the composition of the present invention, together with a stabilizer or a buffer, in water and loading the solution or suspension into ampules or vial unit forms. For sprays, such as aerosols, a propellant for spraying a water-dispersed concentrate or wetting powder may be used in combination with an additive.

In still another aspect to achieve the above objects, the present invention provides an antibiotic comprising the bacteriophage as an active ingredient.

As used herein, the term "antibiotic" means any drug that is applied to animals to kill pathogens, and used herein as a general term for antiseptics, bactericidal agents and antibacterial agents.

The animals are mammals including human.

The bacteriophage of the present invention, unlike the conventional antibiotics, is able to effectively kill Enterotoxigenic *E. coli*, and does not induce drug tolerance or resistance so that it can be provided as a novel antibiotic with a comparatively long life cycle.

In still another aspect to achieve the above objects, the present invention provides a feed additive composition comprising the bacteriophage of the present invention as an active ingredient.

In-feed antibiotics used in livestock and fishery industry are intended to prevent infections. However, most of the currently available in-feed antibiotics are problematic in that they are apt to induce the occurrence of resistant strains and may be transferred to humans as they remain in livestock products. The uptake of such residual antibiotics may make human pathogens resistant to antibiotics, resulting in the spread of diseases. In addition, since there are a variety of in-feed antibiotics, the increasing global emergence of multidrug-resistant strain is a serious concern. Therefore, the bacteriophage of the present invention can be used as an in-feed antibiotic that is more ecofriendly and able to solve the above problems of the known antibiotics.

The feed additive composition of the present invention may be prepared as a composition comprising the bacteriophage, and then mixed with a feed immediately before feeding or directly added on preparation process of a feed. The bacteriophage of the present invention may be contained in the animal feed as a liquid or in a dried form, preferably in a dried powder. The drying process may be performed by air drying, natural drying, spray drying, and freeze-drying, but is not limited thereto. The bacteriophage of the present invention may be added as a powder form in an amount of 0.05 to 10% by weight, preferably 0.1 to 2% by weight, based on the weight of animal feed. The animal feed may also include other conventional additives for the long-term preservation, in addition to the bacteriophage of the present invention.

The feed additive of the present invention may additionally include other non-pathogenic microorganisms. The available additional microorganism may be selected from the group consisting of *Bacillus subtilis* that can produce protease, lipase and invertase, *Lactobacillus* sp. strain that can exert physiological activity and a function of decomposing organic matter under anaerobic conditions, such as in the stomach of cattle, filamentous fungi including *Aspergillus oryzae* (J Animal Sci 43:910-926, 1976) that increases the weight of domestic animals, enhances milk production and helps the digestion and absorptiveness of feeds, and yeast including *Saccharomyce scerevisiae* (J Anim Sci 56:735-739, 1983).

The feed including ΦCJ13 of the present invention may include plant-based feeds, such as grain, nut, food byproduct, seaweed, fiber, drug byproduct, oil, starch, meal, and grain byproduct, and animal-based feeds such as protein, inorganic matter, fat, mineral, single cell protein, zooplankton, and food waste, but is not limited thereto.

The feed additive including ΦCJ13 of the present invention may include binders, emulsifiers, and preservatives for the prevention of quality deterioration, amino acids, vitamins, enzymes, probiotics, flavorings, non-protein nitrogen, silicates, buffering agents, coloring agents, extracts, and oligosaccharides for the efficiency improvement, and other feed premixtures, but is not limited thereto. Further, the supply of drinking water mixed with the bacteriophage of the present invention can reduce the number of ETEC in the intestine, thereby obtaining ETEC-free livestock.

In still another aspect to achieve the above objects, the present invention provides a sanitizer or cleaner comprising the bacteriophage as an active ingredient.

In order to remove ETEC, the sanitizer comprising the bacteriophage as an active ingredient can also be sprayed over and applied to any area where livestock acts, slaughterhouses, spots where livestock died, cooking spaces and cooking facilities, but is not limited thereto. Further, the cleaner comprising the bacteriophage as an active ingredient can be used on the skin and body area of living animals, which are already or potentially contaminated with ETEC.

In still another aspect to achieve the above objects, the present invention provides a method for treating infectious diseases caused by Enterotoxigenic *E. coli*, preferably ETEC, using the bacteriophage or the composition of the present invention.

In detail, the therapeutic method of the present invention includes the step of administering a pharmaceutically effective amount of the bacteriophage or the composition to an individual having infectious diseases caused by pathogenic *E. coli*, preferably ETEC. The bacteriophage or the composition of the present invention may be administered to animals in the form of a pharmaceutical formulation or may be ingested as a mixture with animal feed or drinking water by animals in the form of a feed additive composition. As long as it reaches target tissues, any route, whether oral or parenteral, may be taken for administering the bacteriophage or the composition of the present invention. In detail, the composition of the present invention may be administered in a typical manner via any route such as oral, rectal, topical, intravenous, intraperitoneal, intramuscular, intraarterial, transdermal, intranasal, and inhalation routes. It will be obvious to those skilled in the art that the total daily dose of the bacteriophage or the composition of the present invention to be administered by the therapeutic method should be determined through appropriate medical judgment by a physician. Preferably, the therapeutically effective amount for given patients may vary depending on various factors well known in the medical art, including the kind and degree of the response to be achieved, the patient's condition such as age, body weight, state of health, sex, and diet, time and route of administration, the secretion rate of the composition, the time period of therapy, concrete compositions according to whether other agents are used therewith or not, etc.

MODE FOR THE INVENTION

Hereinafter, the present invention will be described in more detail with reference to Examples. However, these Examples are for illustrative purposes only, and the invention is not intended to be limited by these Examples.

Example 1

Isolation of Bacteriophage Infecting Enterotoxigenic *E. Coli*

Example 1-1

Bacteriophage Screening and Single Bacteriophage Isolation 50 ml of a sample obtained from chicken fecal and environmental samples of Samhwa GPS Breeding Agri., Inc. in the Kwangcheon area, Hong sung-gun, Chung Cheong Province was centrifuged at 4000 rpm for 10 minutes. Then, the supernatant was filtered using a 0.45 μm filter to prepare a sample solution, and used for soft agar overlay method.

In detail, 18 ml of sample filtrate was mixed with 150 μl of Enterotoxigenic *E. coli* (ETEC, SNU0105) shaking culture solution ($OD_{600}$=2) and 2 ml of 10×LB medium (tryptone 10 g/L; yeast extract 5 g/L; NaCl 10 g/L). The mixture was cultured at 30° C. for 18 hours, and the culture solution was centrifuged at 4000 rpm for 10 minutes. The supernatant was filtered using a 0.45 μm filter. 3 ml of 0.7% agar (w/v) and 150 μl of ETEC (SNU105) shaking culture solution ($OD_{600}$=2) were mixed, and plated onto LB plate, and allowed to solidify. 10 μl of the culture filtrate was spread thereon, and cultured for 18 hours at 30° C. to observe formation of phage plaque.

A single plaque represents one bacteriophage and thus, single bacteriophages were intended to be isolated from the plaques. In detail, one phage plaque was added to 400 μl of SM solution (NaCl, 5.8 g/L; $MgSO_4 7H_2O$, 2 g/L; 1 M Tris-Cl (pH 7.5) 50 ml), and left for 4 hours at room temperature to isolate a bacteriophage solution. Subsequently, 100 μl of the bacteriophage solution was mixed with 12 ml of 0.7% (w/v) agar and 500 μl of ETEC (SNU105) shaking culture solution ($OD_{600}$=2), followed by soft agar overlay method on LB plate having a diameter of 150 mm. When lysis was completed, 15 ml of SM solution was added to the LB plate. The plate was left at room temperature for 4 hours to obtain a bacteriophage solution.

The solution was recovered, 1% (v/v) chloroform was added thereto, and mixed well for 10 minutes. The solution was centrifuged at 4000 rpm for 10 minutes. The obtained supernatant was filtered using a 0.45 μm filter to obtain a final sample.

Example 1-2

Large-Scale Cultures and Purification of Bacteriophage

The bacteriophages obtained in Example 1-1 were cultured in large quantities using ETEC (SNU105), and the bacteriophages were purified therefrom.

In detail, ETEC (SNU105) was shaking-cultured, and an aliquot of $1.5\times10^{10}$ cfu was centrifuged at 4000 rpm for 10 minutes, and the pellet was resuspended in 4 ml of SM solution. The bacteriophage of $1.5\times10^{6}$ pfu was inoculated thereto, titrated to MOI (multiplicity of infection) of 0.0001, and left at room temperature for 20 minutes. Subsequently, the solution was inoculated into 150 ml of LB media, and cultured at 30° C. for 5 hours. After completion of the culture, chloroform was added to a 1% (v/v) of final volume, and the culture solution was agitated for 20 minutes. Restriction enzymes DNase I and RNase A were added to a final concentration of 1 μg/ml, respectively. The solution was left at 30° C. for 30 minutes. Then, NaCl and PEG (polyethylene glycol) were added to a final concentration of 1 M and 10% (w/v), respectively and left at 4° C. for additional 3 hours. The solution was centrifuged at 4° C. and 12000 rpm for 20 minutes to obtain a pellet. The pellet was resuspended in 5 ml of SM solution, and left at room temperature for 20 minutes. 4 ml of chloroform was added thereto and mixed well, followed by centrifugation at 4° C. and 4000 rpm for 20 minutes. The supernatant was filtered using a 0.45 μm filter, and the bacteriophage was purified by glycerol density gradient ultracentrifugation (density: 40%, 5% glycerol at 35,000 rpm and 4° C. for 1 hour).

The present inventors designated the bacteriophage as "Bacteriophage ΦCJ13", in which the bacteriophage having a specific bactericidal activity against ETEC and the above characteristics was isolated from fecal samples at chicken slaughterhouses, and deposited at the Korean Culture Center of Microorganisms (361-221, Honje 1, Seodaemun, Seoul) on Nov. 7, 2011 under accession number KCCM11217P.

Example 2

Examination on ΦCJ13 Infection of *E. Coli*

To analyze the bacteriophage ΦCJ13 purified in Example 1 for lytic activity on *E. coli* species other than ETEC (SNU105), attempts were made of cross infection with other *E. coli* species.

In detail, two kinds of ETEC (SNU105) and ETEC (CANRO8) and eight kinds of non-pathogenic *E. coli* (DH5a, MC4100, Rosetta (DE3), GM2929, K12G, W3110, BL21 (DE3), Tuner (DE3)) were cultured to obtain culture solutions. Each culture solution and the purified ΦCJ13 were used to perform soft agar overlay method, and the formation of phage plaques thereof was examined (Table 1).

TABLE 1

ΦCJ13 Infection of *E. coli*

| Strain name | Phage plaque formation |
|---|---|
| ETEC(SNU105) | ○ |
| ETEC(CANRO8) | ○ |
| *E. coli* DH5a | X |
| *E. coli* MC4100 | X |
| *E. coli* Rosetta(DE3) | X |
| *E. coli* GM2929 | X |
| *E. coli* K12G | X |
| *E. coli* W3110 | X/○ |
| *E. coli* BL21(DE3) | X |
| *E. coli* Tuner(DE3) | X |

* 'SNU' source: College of Veterinary Medicine, Seoul National University
* 'CAN' source: University of Guelph in Canada As shown in Table 1, the bacteriophage ΦCJ13 purified in Example 1 did not show lytic activity on non-pathogenic *E. coli.*

Example 3

Morphology of ΦCJ13

Figure 1:
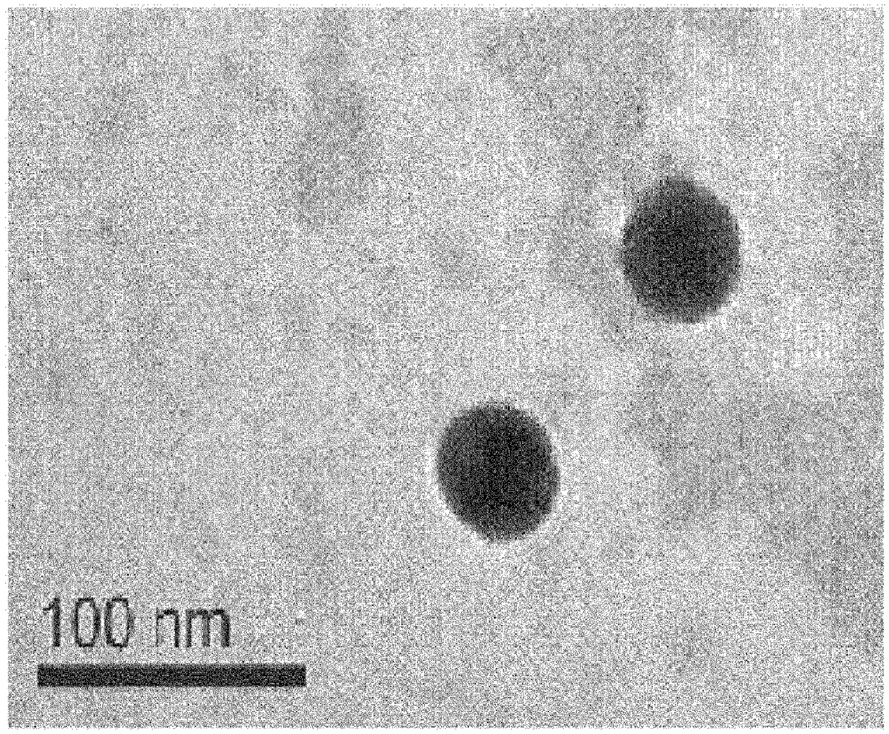
FIG. 1 is an electron microscope image of ΦCJ13.

The ΦCJ13 purified in Example 1 was diluted in a 0.01% gelatin solution, and then fixed in a 2.5% glutaraldehyde solution. The sample was dropped onto a carbon-coated mica plate (ca. 2.5×2.5 mm), adapted for 10 min, and washed with sterile distilled water. A carbon film was mounted on a copper grid, stained with 4% uranyl acetate for 30-60 seconds, and dried. Examination under a JEM-1011 transmission electron microscope (at 80 kV, magnification of ×120,000~×200,000) was performed (FIG. 1). FIG. 1 is an electron microscopy photograph of ΦCJ13. It was found that the purified ΦCJ13 belongs to the family Podoviridae of morphotype, characterized by an isometric capsid and no tail.

Example 4

Analysis of Total Genomic DNA Size of ΦCJ13

Genomic DNA was extracted from the ΦCJ13 purified in Example 1.

Figure 2:
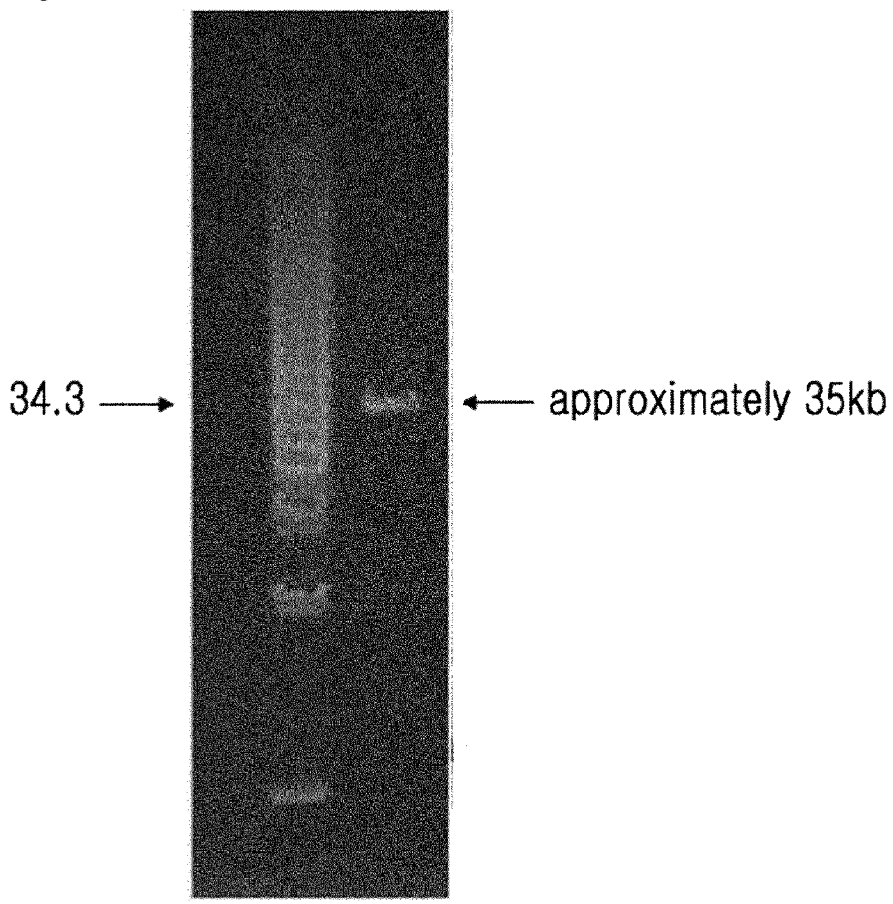
FIG. 2 is the result of PFGE of the isolated bacteriophage ΦCJ13.

In detail, to the purified ΦCJ13 culture solution were added 20 mM EDTA, 50 μg/m1 proteinase K, and 0.5% (w/v) SDS, followed by incubation at 50° C. for 1 hour. An equal volume of phenol (pH 8.0) was added and mixed well. After centrifugation at room temperature and 12,000 rpm for 10 minutes, the supernatant was mixed well with an equal volume of PC (phenol:chloroform=1:1). Another centrifugation was performed at room temperature and 12,000 rpm for 10 minutes. Then, obtained supernatant was mixed with an equal volume of chloroform, followed by centrifugation at room temperature and 12,000 rpm for 10 minutes. The obtained supernatant was mixed with 10% (v/v) of 3 M sodium acetate and then two volumes of cold 95% ethanol, and left at −20° C. for 1 hour. After centrifugation at 0° C. and 12,000 rpm for 10 minutes, a pellet was obtained, and the DNA pellet was dissolved in 50 μl of TE buffer (Tris-EDTA (pH 8.0)), and its concentration was measured. 1 μg of DNA was loaded onto 1% PFGE (pulse-field gel electrophoresis) agarose gel, and electrophoresed at room temperature for 20 hours using a BIORAD PFGE system program 7 (size range 25-100 kb; switch time ramp 0.4-2.0 seconds, linear shape; forward voltage 180 V; reverse voltage 120 V) (FIG. 2). FIG. 2 is the result of electrophoresis of genomic DNA of the bacteriophage ΦCJ13, indicating its size of approximately 35 kbp.

Example 5

Protein Pattern Analysis of ΦCJ13

15 μl of a purified ΦCJ13 solution at a titer of $10^{10}$ pfu/ml was mixed with 3 μl of a 5×SDS sample solution, and heated for 5 minutes. 15% SDS-PAGE was performed (FIG. 3). FIG. 3 is the result of SDS-PAGE of the bacteriophage ΦCJ13. As shown in FIG. 3, the major proteins were detected at 43 kDa, 38 kDa, 34 kDa and 33 kDa.

Example 6

Genetic Analysis of ΦCJ13

For the genetic analysis of the ΦCJ13 purified in Example 1, 5 μg of the genomic DNA of ΦCJ13 was double digested with the restriction enzymes EcoRV, ScaI and NruI, and PvuII, HincII and StuI. The vector pCL1920 (Promega) was digested with the restriction enzyme SmaI, and then treated with CIP (calf intestinal alkaline phosphatase). The digested genomic DNA was mixed at a ratio of 3:1 with the vector, and ligated at 16° C. for 5 hours. The resulting recombinant vector was transformed into *E. coli* DH5α which was then plated on an LB plate containing ampicillin and X-gal (5-bromo-4-chloro-3-indolyl-beta-D-galactopyranoside) for selection of blue/white colonies. Two colonies were selected, and cultured with shaking for 16 hours in a culture medium containing ampicillin. Then, plasmids were extracted using a plasmid purification kit (Solgent).

The cloning of the plasmids was confirmed by PCR using primer sets of M13 forward and M13 reverse and selection was made only of insert having a size of 1 kb or longer. Their base sequences were analyzed using the primer sets of M13 forward and M13 reverse (Table 2).

TABLE 2

Comparison of Sequence Homology between ΦCJ13 and Other Bacteriophages

| SEQ ID NO: | Organic | Protein | Quary | Identity | E-value |
|---|---|---|---|---|---|
| 1 | Enterobacteria phage EcoDS1 | gp19 | 38-388 | 116/117 (99%) | 7.00E−53 |
| | Enterobacteria phage EcoDS1 | gp19.5 | 727-52 | 38/38 (100%) | 5.00E−05 |

TABLE 2-continued

Comparison of Sequence Homology between ΦCJ13 and Other Bacteriophages

| SEQ ID NO: | Organic | Protein | Quary | Identity | E-value |
|---|---|---|---|---|---|
| 2 | Enterobacteria phage K1F | tail tube(gp 12) | 966-37 | 306/310 (99%) | 4.00E−165 |
| 3 | Enterobacteria phage K1F | tail tubular protein A(gp 11) | 360-31 | 109/110 (99%) | 8.00E−44 |
| | Enterobacteria phage EcoDS1 | major capsid protein (gp 10A) | 807-932 | 50/50 (100%) | 3.00E−49 |
| 4 | Enterobacteria phage K1F | endo-N-acylneuraminidase | 303-40 | 88/88 (100%) | 5.00E−42 |
| | Enterobacteria phage EcoDS1 | internal virion protein D(gp 16) | 1169-371 | 128/129 (99%) | 3.00E−110 |
| 5 | Enterobacteria phage P1 | putative lipoprotein (Plp) | 510-136 | 124/125 (99%) | 3.00E−62 |
| | Enterobacteria phage P1 | gene upstream of plp (Upl) | 702-514 | 63/63 (100%) | 8.00E−28 |
| | Enterobacteria phage P1 | tellurite or colicin resistnce/inhibition of cell-division (TciA) | 908-1140 | 50/55 (91%) | 8.00E−21 |
| 6 | Enterobacteria phage EcoDS1 | internal virion protein D (gp 16) | 1066-284 | 225/264 (86%) | 1.00E−118 |
| | Enterobacteria phage EcoDS1 | gp17 | 216-37 | 60/60 (100%) | 2.00E−25 |

Example 7

Design of ΦCJ13-Specific Primer Sequences

In order to identify ΦCJ13, ΦCJ13-specific primers were designed.

In detail, the primer sets of SEQ ID NOs: 7 and 8 and SEQ ID NOs: 9 and 10 were constructed on the basis of SEQ ID NOs: 1 and 2, respectively. Further, the primer sets of SEQ ID NOs: 11 and 12, SEQ ID NOs: 13 and 14. SEQ ID NOs: 15 and 16, and SEQ ID NOs: 17 and 18 were constructed on the basis of SEQ ID NOs: 3, 4, 5 and 6, respectively. PCR was performed. 0.1 μg of the genomic DNA of bacteriophage and 0.5 pmol of each primer were added to a pre-mix (Bioneer), and the final volume was adjusted to 20 mL. PCR was performed with 30 cycles of denaturation; 94° C. 30 seconds, annealing; 60° C. 30 seconds, and polymerization; 72° C., 1 minute. As a result, the PCR products thus obtained had a size of approximately 170 bp, 180 bp, 200 bp, 205 bp, 240 bp and 200 bp, with the primer sets of SEQ ID NOs: 7 and 8, SEQ ID NOs: 9 and 10, SEQ ID NOs: 11 and 12, SEQ ID NOs: 13 and 14, SEQ ID NOs: 15 and 16, and SEQ ID NOs: 17 and 18, respectively.

Example 8 pH Stability of Bacteriophage

Figure 4:
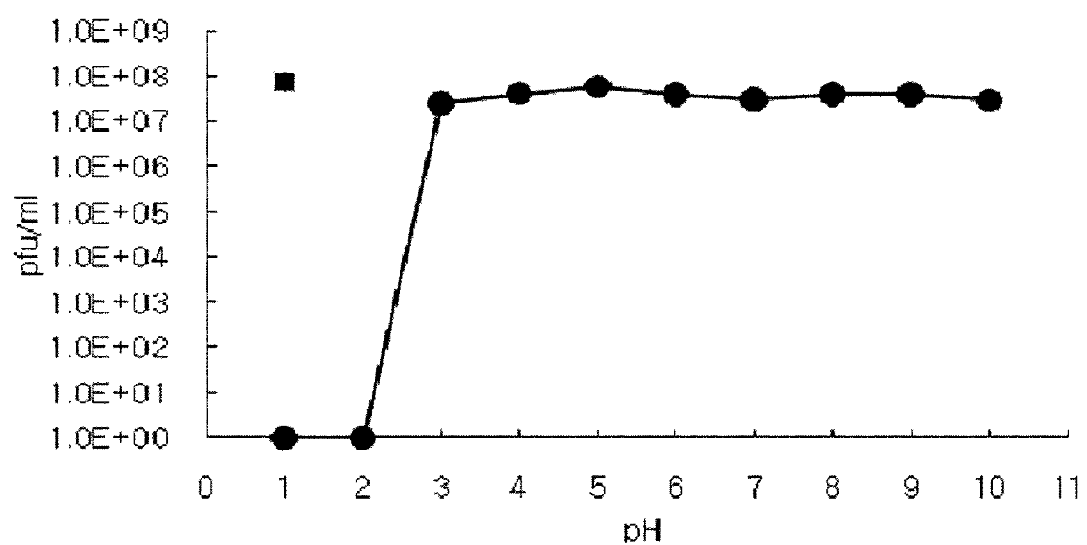
FIG. 4 is the result of an acid-resistance assay on the bacteriophage ΦCJ13.

In order to determine whether ΦCJ13 survives with stability under the low pH environment in the stomach of pig, ΦCJ13 was assayed for stability in a wide range of pH (pH 2.1, 2.5, 3.0, 3.5, 4.0, 5.5, 6.4, 6.9, 7.4, 8.2, 9.0, 9.8 and 11.0). Various pH solutions (sodium acetate buffer (pH 2.1, pH 4.0, pH 5.5, and pH 6.4), sodium citrate buffer (pH 2.5, pH 3.0, and pH 3.5), sodium phosphate buffer (pH 6.9 and pH 7.4) and Tris-HCl (pH 8.2, pH 9.0, pH 9.8 and pH 11.0)) were prepared to have a concentration of 0.2 M. 90 μl of each pH solution was mixed with 10 μl of a bacteriophage solution ($1.0\times10^{11}$ pfu/ml) to give each pH solution a concentration of 1 M, followed by incubation at room temperature for 2 hours. The reaction solution was serially diluted, and 10 μl of each dilution was cultured at 37° C. for 18 hours by a soft agar overlay method to determine the titers of the phage lysates (FIG. 4). FIG. 4 is the result of acid-resistance assay on the bacteriophage ΦCJ13. As shown in FIG. 4, the bacteriophage ΦCJ13 did not lose its activity and remained stable between pH 3.0 and pH 10.0, compared to the control group.

Example 9

Heat Stability of Bacteriophage

For use as a feed additive, the bacteriophage was assayed for stability to the heat generated during a formulation process. In this regard, 100 μl of a ΦCJ13 solution with a titer of $1.0\times10^{8}$ pfu/ml was incubated at 40° C., 50° C., 60° C., and 70° C. for 0 minute, 30 minutes, 60 minutes and 120 minutes. The solution was serially diluted, and 10 μl of each dilution was cultured at 30° C. for 18 hours by a soft agar overlay method to determine the titers of phage lysates (FIG. 5). FIG. 5 is the result of heat-resistance assay on the bacteriophage ΦCJ13. As shown in FIG. 5, the bacteriophage ΦCJ13 maintained its activity even though exposed at 50° C. up to 2 hours, but its activity was reduced according to time, when exposed at 60° C. for 30 minutes or more.

Example 10

Infection Spectrum of Bacteriophage on Wild-Type ETEC

ΦCJ13 was assayed for lytic activity against 10 ETEC strains of the wild-type, obtained from College of Veterinary Medicine, Seoul National University and University of Guelph in Canada, in addition to ETEC (SNU105) used in the experiment. 150 μl of each strain shaking culture solution ($OD_{600}$=2) was mixed, and 10 μl of ΦCJ13 solution having a titer of $10^{8}$ pfu/ml was dropped and cultured at 30° C. for 18 hours using a soft agar overlay method to monitor the formation of plaques (Table 3).

TABLE 3

| Formation of phage plaques for Korean wild-type ETEC strains | |
|---|---|
| Strain name | Phage plaque formation |
| ETEC SNU105 | ○ |
| ETEC SNUF4 | ○ |
| ETEC SNU162 | ○ |
| ETEC SNU160 | ○ |
| ETEC SNUJG280 | ○ |
| ETEC SNU107 | ○ |
| ETEC SNU2618 | ○ |
| ETEC SNU193 | ○ |
| ETEC CAN3220 | ○ |
| ETEC SNUR08 | ○ |

* 'SNU' source: College of Veterinary Medicine, Seoul National University
* 'CAN' source: University of Guelph in Canada As shown in Table 3, the bacteriophage showed infectivity on ETEC O-serotype O149 (SNU107, SNUF4, SNUJG280, CAN3220, SNUR08) which is the most common cause of diarrhea in pigs, and also F-serotype K88 (SNU105, SNU107, SNU160, SNU162, SNU193, SNUF4, CAN3220, SNUR08, SNUJG280), K99 (SNU2618) and thus, it can be expected that the bacteriophage will show excellent efficiency when applied.

Example 11

Availability of ETEC Bacteriophage in Feed for Weaned Piglets 50 weaned piglets (Landrace X Yorkshire) which were 25 day-old and determined as ETEC antigen-negative healthy by examination of gross and clinical finding (diarrhea, depression, etc.) and fecal PCR were divided according to weight, sex. The experiment was performed for 14 days.

First, ETEC strain was inoculated in TSB, and cultured at 37° C. for 18 hours. The culture solution was diluted with PBS (PH 7.2) and a titer was adjusted to $10^8$ pfu/ml, and orally administered into 5-week pigs using a sonde at 7 days after initiation of the experiment. From the initial day of the experiment, the bacteriophage-treated groups were fed with a feed mixture of 1 g of bacteriophage ($10^6$ pfu/g or $10^8$ pfu/g) per 1 kg of feed twice a day at predetermined times each morning and afternoon. The bacteriophage control group was fed with a standard feed only at the same time (FIGS. 6 and 7)

Figure 6:
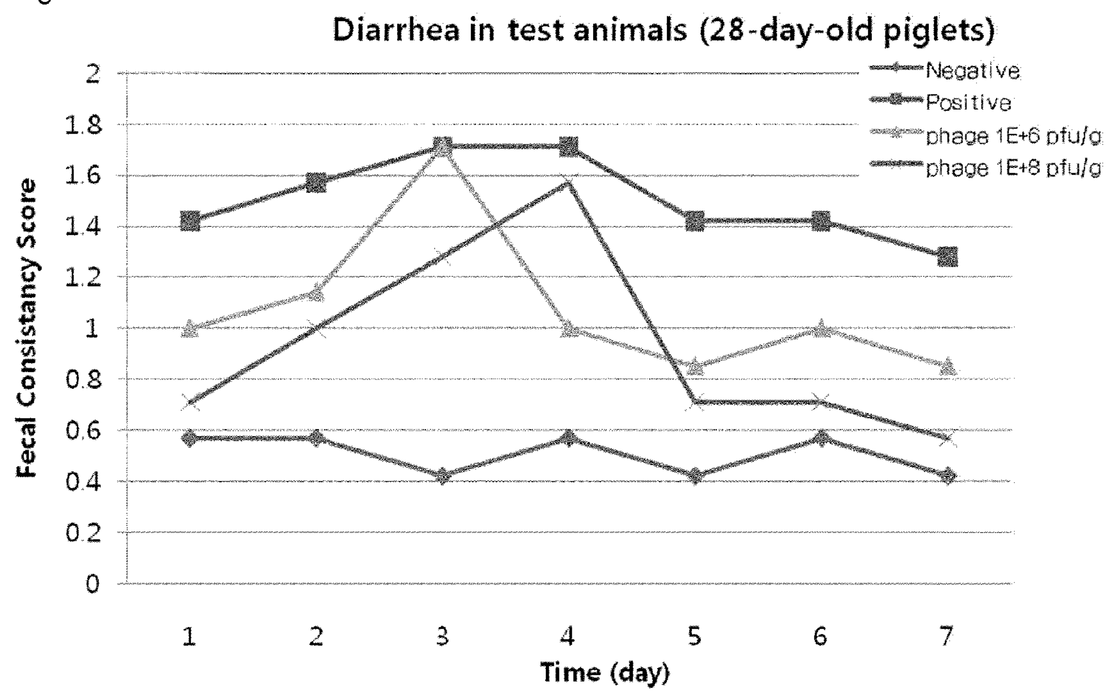
FIG. 6 is the result of comparing fecal consistency scores between weaned piglets fed with a standard feed supplemented with ΦCJ13 and weaned piglets fed with a standard feed only, after force feeding of ETEC.

First, FIG. 6 is the result of comparing fecal consistency scores between weaned piglets fed with a standard feed supplemented with ΦCJ13 and piglets fed with a standard feed only, after force feeding of ETEC. The weaned piglets that were not force-fed with ETEC strain were defined as a negative control group. The weaned piglets that were force-fed with ETEC strain ($1.0\times10^8$ pfu/me) and fed with a standard feed only were defined as a positive control group. Starting at 7 days before feeding of ETEC strain, the experimental groups were fed with the feed supplemented with the bacteriophage. The weaned piglets fed with the feed supplemented with the bacteriophage showed lower fecal consistency scores than the groups fed with the standard feed only. As shown in FIG. 6, fecal consistency scoring was based on the following index used by Sherman et al. (1983) (normal feces, 0; soft feces, 1; fluid diarrhea, 2; severe diarrhea, 3). The positive control group fed with the ETEC bacteriophage (fed with a standard feed after feeding of ETEC) showed high fecal consistency scores, but the experimental group fed with the feed supplemented with the bacteriophage showed high scores until 3-4 days, and then normalized.

Figure 7:
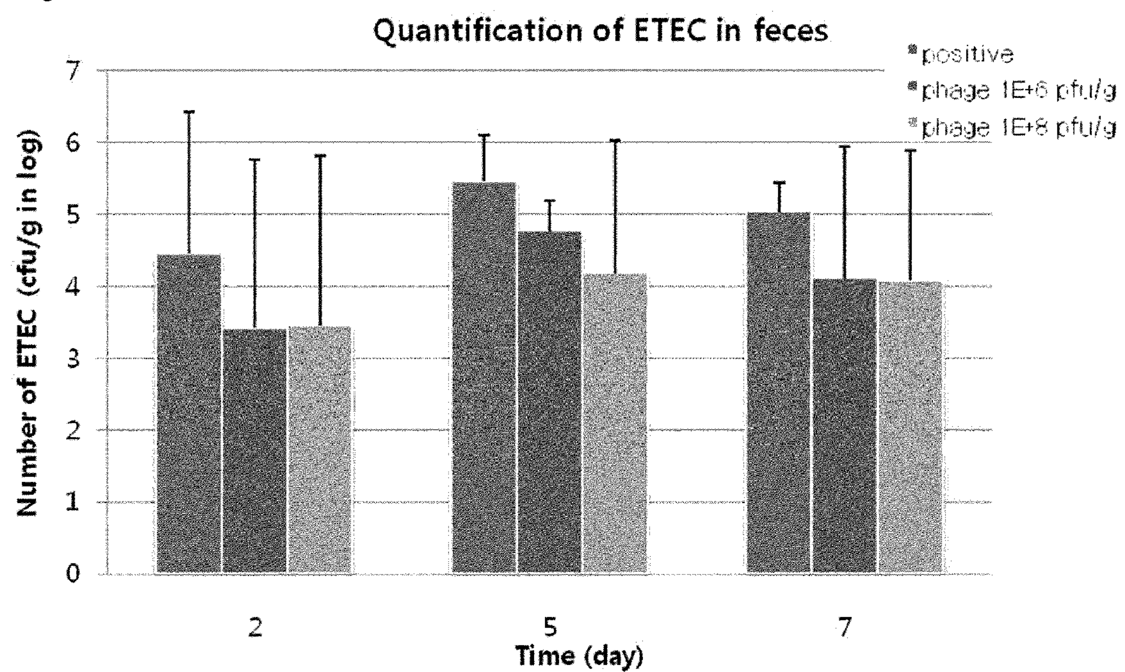
FIG. 7 is the result of real time PCR for the quantification of ETEC in feces.

FIG. 7 is the result of Real time PCR for the quantification of ETEC in feces. A lower amount of ETEC was observed in the feces of the weaned piglets fed with the feed supplemented with the bacteriophage than in that of the weaned piglets fed with the standard feed only. As shown in FIG. 7, the result of Real time PCR for the quantification of ETEC in feces showed that the feces of the experimental group fed with the bacteriophage had lower ETEC content than the positive control group.

Example 12

Analysis on Intestinal Villus Length of Weaned Piglets

Typically, piglets exposed to ETEC are characterized in that they have short intestinal villus than normal piglets, and show abnormal water absorption, resulting in diarrhea (Gaastra W. et al., Microbial Rev. 46,129-161, 1982). On the basis of this fact, effects of ΦCJ13 on the intestinal villus length of piglets exposed to ETEC were examined.

After completion of the experiment of Example 11, the experimental piglets were euthanized, and each 3 cm of the duodenum, jejunum, ileum and colon tissues was collected, and fixed in 10% normal formalin for 48 hours. After general tissue treatment procedure, the tissues were embedded in paraffin, and sectioned at 3-μm thickness. The tissue sections were deparaffinized and rehydrated, and then stained with H&E (hematoxylin and eosin). Next, the height of villus and the length of crypt were measured to analyze the intestinal morphology. At this time, for measurement of the height of villus and the length of crypt, the images from the stained duodenum, jejunum, and ileum tissue sections were acquired from left to right and top to bottom using spot diagnostic insight (Olympus, USA). The height of villus (V), the depth of crypt (C), and a ratio of the height of villus to the depth of crypt (V/C ratio) were measured, followed by statistical analysis (Table 4).

TABLE 4

Analysis on intestinal villus length

| | Population of weaned piglets | | | | |
|---|---|---|---|---|---|
| Location in intestine | Negative group | Positive group | Phage (1E+6) | Phage (1E+8) | P value |
| Duodenum | | | | | |
| Length of villus (m) | 540.9 | 305.6 | 334.5 | 322.9 | <.0001 |
| Depth of crypt (m) | 287 | 345.3 | 343.5 | 316.2 | 0.0013 |
| V/C ratio(m) | 0.483a | 0.239b | 0.501b | 0.401b | — |
| Jejunum | | | | | |
| Length of villus (m) | 75.9 | 52.5 | 54.7 | 128.5 | 0.0013 |
| Depth of crypt (m) | 233.9 | 258 | 264 | 210.8 | 0.169 |
| V/C ratio(m) | 1.798 | 0.885 | 1.013 | 1.747 | 0.0005 |
| Ileum | | | | | |
| Length of villus (m) | 406 | 228 | 282.7 | 402 | <.0001 |
| Depth of crypt (m) | 256.0a | 307.2a | 244.4a | 222.3a | — |
| V/C ratio(m) | 1.640a | 0.804c | 1.235b | 1.868a | — |

a, b, c: mean values are clearly distinguishable above the standard deviation range As shown in table. 4, the ETEC challenge group (positive group) had shorter villi and deeper crypts in the duodenum than the non-challenge, negative group ($P<0.05$). The bacteriophage-treated phage (1E+8) group had villi length of 128.5 μm in the jejunum, indicating 52.5 μm longer than the ETEC challenge positive group ($P<0.05$). There was no significant difference in the depth of crypts. The bacteriophage-treated phage (1E+6) and (1E+8) groups had a V/C ratio of 1.013 and 1.747, respectively, indicating significantly higher ratio than 0.885 of the ETEC challenge positive group. The phage (1E+8) group showed a higher ratio than the phage (1E+6) group ($P<0.05$). The phage (1E+6) group and the phage (1E+8) group had had a V/C ratio of 1.235 and 1.868 in the ileum, respectively, indicating that significantly higher ratio than 0.804 of positive group ($P<0.05$). Considering that healthy pigs have long villi, the effects of the bacteriophage were found to be significant.

The invention claimed is:

1. A method for restraining or retarding progress of, or treating, an infectious disease caused by Enterotoxigenic *Eschericial coli*, comprising the step of administering a bacteriophage identified by Accession No. KCCM11217P to a mammal in need of treatment.

2. The method according to claim 1, wherein the mammal is a pig.

3. A method for restraining or retarding progress of, or treating, an infectious disease caused by Enterotoxigenic *Escherichia coli*, comprising the step of administering a composition comprising a bacteriophase identified by Accession No. KCCM11217P as an active ingredient to a mammal in need of treatment.

4. The method according to claim 3, wherein the infectious disease caused by Enterotoxigenic *Escherichia coli* is colibacillosis.

5. The method according to claim 3, wherein the mammal is a pig.

* * * * *

SEQUENCE LISTING

<160> NUMBER OF SEQ ID NOS: 18

<210> SEQ ID NO 1
<211> LENGTH: 824
<212> TYPE: DNA
<213> ORGANISM: unknown
<220> FEATURE:
<223> OTHER INFORMATION: Bacteriophage

<400> SEQUENCE: 1
gcacacgatg accgacttga tgcgcttgct ataggtgtac agttcttcgt tgagtctatg 60
gctaaggatg ccaacaaagg cgaacgtgaa gtcactgagg agtggctgga ggaacagatg 120
gagaacccac ggaaaggctt cgagtccatc cacactgagt tctgggacaa tggggtccgg 180
gtaactcacg atacggacga cgagctggga ctagggtcat acgttacgtt ccactagctg 240
aatgaataat tataggtgaa agctgcatga atacgcggtt agtaacctat agttactacc 300
agtctaacct actgttttac aaggagtttg gacttaacta tcactatagg gaagaccccc 360
ggttacttat agtattactg tagtgaatat acatatgcag actttatgca agaccttagg 420
aggcagactc cgagttctta cctaaggctt gcaccgatgg aaggagggtg atattaatca 480
taatccctcc aatacagata gtaaagacca tagatacagg aggtatgtag catatggcaa 540
agaccaaagc tgtacttaaa gctctggcga ccaatcgagc tacatacagg tttcttgctg 600
ctgttctact tgctgctggc gttactgctg gaagtcagtg ggtcgggtgg gtcgagactc 660
tcgtatgttc tctggtctct cagtgtaatt aacgcaatca tggtaacgat tcatgagcgg 720
aagacctaag gtcagtacgt ggataaagac tcactctact gaccttagct actatagtca 780
aggactttag gtaacactat agcagctcat ggtctatcca aagg 824

<210> SEQ ID NO 2
<211> LENGTH: 1035
<212> TYPE: DNA
<213> ORGANISM: unknown
<220> FEATURE:
<223> OTHER INFORMATION: Bacteriophage

<400> SEQUENCE: 2
gagctcggta cccgacgcag atgtagttct cagtccctgt accttgaatg tcaaacaccc 60
cgttagggat ataggacagt acgtggccag tggtatcatc cgcatccttc acgtcagaca 120
catctgctac agcgaagtat cgcttaatgc tggtgaatga cccacgaggc gctgagaaga 180
agactgagcg tcctacagcg aacggtctgg cattatcgcc taaggcaaac tctgagccta 240
catcaagctg gatagacttc gaggtaagga ccccagagct tgtcatcacg aactgaacct 300
catccgacca aagtagtagc tgctcactaa acggaacggc atacttaagg attgagattc 360
gagggtgact tacagctaca tcaatagggt catcatcact cagtgtcgcc acactcttag 420
ggaagaacgc aaagtagctt gctgaacggc tcattattac gttctcgcct gacaagaacc 480
ccagcctatt cctgtagaag aacacatcgt taatcgtggc atccacgaag ctaggcatag 540

```
ggtttgtgtc atcattacca gcaccacgct tagaccagtc cagagtcttg aactcaaagg    600

agccgtcgga ttgcctaacc agagcatggg gcattgtggt gttatcgaac ccagtgacca    660

ctcccgtccc tactgtctcc ttccacgtct tagtgttgga gtcatacatc acgtaatatt    720

catcggcgct actgtttgtc tcaccttgaa tcttaatgat gtacccattt ggagctgcaa    780

gaggcaactt agagattgtt tgcaccgtgt cgagtactgg actgattagc tggttagcgt    840

agccatcctc cgtctccact gagttaatgt cagtccctga aggggcagtg attaacagga    900

agccagaccc aaggtcaaac gtgaaggtag gataggcagc aacagaaggt ctctcagagc    960

tgcaccaatg gcttgagcgt cggggatcct ctagagtcga cctgcaggca tgcaagcttg   1020

gcgtatcatg gtcat                                                    1035
```

<210> SEQ ID NO 3
<211> LENGTH: 971
<212> TYPE: DNA
<213> ORGANISM: unknown
<220> FEATURE:
<223> OTHER INFORMATION: Bacteriophage
<220> FEATURE:
<221> NAME/KEY: misc_feature
<222> LOCATION: (1)...(971)
<223> OTHER INFORMATION: n = A,T,C or G

<400> SEQUENCE: 3

```
acaggtatcc gcccatgttg ctataatagc tggtggcccc ggcagtcatt acacgaaggt     60

atgacggtaa gaatcgaatc ctattgtctt ggacatcagg tgtcaggacg gcagcttcgt    120

tgatattaaa gttccagcct ttagcttgga cctgacgatt gacgcgatgc agtatacgtt    180

gagcgttaga gacgtcagcg ttcccctcgt caagctgtag gactgctggt tcaccgatag    240

cagctaacat atcgttgatg gcatctaagt catcgttagc gttcagtgga atgtattgag    300

ccatactccc tcctatctgt cgtaaggact gcatggtccg gttaataata tagtcgccca    360

gaaactaaca aatagtccca aggctgttag taagtaaaac ataatcatcc caactttaag    420

caaaaaaaaa acccctcaag cacccgaagg cacccaaggg gtttcaatta gttgttggac    480

tcanccagtt tagcggccct gttcgcagca cgagtacgcg cagctttctg ttgaggagtt    540

aaattctcct cttcaggtgc agccgctact gtagcgacgt taggttggct aaaggtgctt    600

acgccgctgg gctgaaaacc agtgcgccag cagcttcagg acgcagacca ccgtgaccca    660

tagcgtattt accaacaatc aggtcgccct gagcatcgac gtcacggtca cgttccagcg    720

ccaagtcacg cagcttcaca gtacccacag canacggtga gagaacaggc ccacaacgtt    780

gtccatagca actttaacgt cgccagtagc agttgccggg aatgcgtgtt tctgaccgga    840

agcgatagag ataccatcgt caccacgggt ctcacagcgc caccctgtac cagatgcgga    900

acttcaacaa caacgaagcc catcacgtta cggatgttac cagtctctgg gtcaatcagc    960

gcagcatagt t                                                         971
```

<210> SEQ ID NO 4
<211> LENGTH: 1095
<212> TYPE: DNA
<213> ORGANISM: unknown
<220> FEATURE:
<223> OTHER INFORMATION: Bacteriophage
<220> FEATURE:
<221> NAME/KEY: misc_feature
<222> LOCATION: (1)...(1095)
<223> OTHER INFORMATION: n = A,T,C or G

<400> SEQUENCE: 4

```
attcctgaag tctaccacta agtcagttcc agtctgacgg tgaatacgaa cgatgtcgaa     60
acctgattgg tcaaccaaca tctcaatcat cgttggatta aggaatcggt aatctcgacc    120
aacttcaagt acacggttca gggtagggtt agagctattc accagcgtaa caacaacaaa    180
cgttctggct aggtagtcga actcaatcct gtactgagtg tttcctgaag ggaattgtgt    240
aatcgtggac attatgcctc ctttgtgatt taaacggaga cctatggtag cgcctccagt    300
ttcctatagt gatagtttag tccttgatgt ggatgccttg ctcctcaaac gttccaagca    360
atagcttctg ggtaatgggg tcgttcggaa ccagttcacg gaacgtatta tacatcccgg    420
tcatgtagtc tcgctcgttt acccgagtgt cggccttcag gtagccagcc aagttgtaag    480
ccgaagcgcc aacgttagca gcatatccga aagctggaac ctgctccaag aagttaccaa    540
caacattcat cacggggtca cttgtagctg caccatacgc gatggcacgt tcaggctgct    600
ctgtaggcga acgaggtagg atagacgaac ggagcatctt agtgtcctca tacccagcga    660
tgccacccag aatgttagct accccaagtg gaccacccag atgtgaaact acgggacaga    720
gccgcataac caatcatcgt cgggtcaaga gcttgcttga ggtattcacg gtctcgacca    780
tcctgcatag cgtaagcctt gacgtgagct tgagccatat agtagatacc agccagaccc    840
atagacatca cggtagatag agcagcatcc atcgctcggt tgttcttcgt ggcgttatag    900
aaggttcgca tggttcgccc attgatggac ttgatgacga agttccttaa actgaaggac    960
agtcttagcg agagggccat aagcttgcat ccatgttaag acagctatga ggtcgtagta   1020
cgtttcatcc agcaatggtg tcaaccatac gccaacaggt caatancctt gggtcctgaa   1080
ctgaacgact tctta                                                    1095
```

<210> SEQ ID NO 5
<211> LENGTH: 979
<212> TYPE: DNA
<213> ORGANISM: unknown
<220> FEATURE:
<223> OTHER INFORMATION: Bacteriophage

<400> SEQUENCE: 5

```
cgatggttca aatccatcca ccatcgccaa tgccggttta gctcagttgg tagagcgcct     60
gccttgtaag caggatgtca gcggttcgag tccgttaatc ggcaccagca caacaggtaa    120
gggtattttg cgacgtcgga gatcgccgag cttggcagag ggttcgaatc cctacgaagt    180
acccttaccg ttgtgatgaa gtgcagctct ttgaagcaac cagaagataa gcatctggct    240
tcacaacata aaccgcagga acgaccaata aacggtagtc cgtatggaga acaccccgtt    300
gaggaagagg cctggccgga accgtaaccg gcactacaac gttgagaaca ctggcgtaac    360
ggggtcatat cccaatctac gaataaatgt tgcgttgcag cgtgacaacc agtgttctca    420
acattgtggt gaatgcacag gctgatgtgc cgcaactaca gtagtgcgcg ctttgcgggg    480
cttgctacaa ccctgtgtcg gagttcagca ccgaccatca cagtttgatt ctctggcatg    540
agcataacgc tgaaataagt ccagtctggt gcggcccgat cacccgccgt tagctccacg    600
aaacggagca cgtaacaggt aagagcattc tcctgtaacg ggttcatatc ccaatctaca    660
ggtccaccaa gaatgctctt tccgttgcgg tgaatgcggc taagcgcacg cggggaaatg    720
gttatatctg tccattattt ctccttgttt ccacgtccac ggtggataac cagccaaagg    780
acaccgggag gcacccggca ccgcaacctt atttcccaac cagtaatgag gttaataaat    840
gctcggcatt ctcaaaagaa attccgcaaa gcggctggcg gagtcaagaa gatggaaaac    900
```

```
cgtgatgccg tggaagcgac tgtctggggc gcatattcca ttgcatactc tgacggcacc     960

tgcgatgcga aagaaattg                                                  979


<210> SEQ ID NO 6
<211> LENGTH: 979
<212> TYPE: DNA
<213> ORGANISM: unknown
<220> FEATURE:
<223> OTHER INFORMATION: Bacteriophage

<400> SEQUENCE: 6

catcgttgga ttaaggaatc ggtaatctcg accaacttca agtacacggt tcagggtagg      60

gttagagcta ttcaccagcg taacaacaac aaacgttctg gctaggtagt cgaactcaat     120

cctgtactga gtgtttcctg aagggaattg tgtaatcgtg gacattatgc ctcctttgtg     180

atttaaacgg agacctatgg tagcgcctcc agtttcctat agtgatagtt tagtccttga     240

tgtggatgcc ttgctcctca aacgttccaa gcaatagctt ctgggtaatg gggtcgttcg     300

gaaccagttc acggaacgta ttatacatcc cggtcatgta gtctcgctcg tttacccgag     360

tgtcggcctt caggtagcca gccaagttgt aagccgaagc gccaacgtta gcagcatatc     420

cgaaagctgg aacctgctcc aagaagttac caacaacatt catcacgggg tcacttgtag     480

ctgcaccata cgcgatggca cgttcaggct gctctgtagg cgaacgaggt aggatagacg     540

aacggagcat cttagtgtcc tcatacccag cgatgccacc cagaatgtta gctaccccaa     600

gtggaccacc cagatgtgaa ctacgggaca gagccgcata accaatcatc gtcgggtcaa     660

gagcttgctt gaggtattca cggtctcgac catcctgcat agcgtaagcc ttgacgtgag     720

cttgagccat atagtagata ccagccagac ccatagacat cacggtagat agagcagcat     780

ccatcgctcg gttgttcttc gtggcgttat agaaagttcg catggttcgc ccattgatgg     840

acttgatgac gaagttctta aactgaaagg acagtcttag cgagagggcc ataagccttg     900

gcatccatgt tagacagctt atgaggtcgt agtaacgttt catcagcgat ggtgtcaccc     960

atacgccaca gtccatagc                                                  979


<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7

tgaaagctgc atgaatacgc                                                  20


<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8

tgcctcctaa ggtcttgcat                                                  20


<210> SEQ ID NO 9
<211> LENGTH: 20
<212> TYPE: DNA
<213> ORGANISM: Artificial Sequence
<220> FEATURE:
```

<223> OTHER INFORMATION: Primer

<400> SEQUENCE: 9
ggattgagat tcgagggtga 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgccacgatt aacgatgtgt 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcttcacagt acccacagca 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtaacgtgat gggcttcgtt 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
atcacggggt cacttgtagc 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ctcttgaccc gacgatgatt 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
accgtaaccg gcactacaac 20

-continued

```
<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16

tttcagcgtt atgctcatgc                                                20


<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17

atcacggggt cacttgtag                                                 19


<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18

ctcttgaccc gacgatgatt                                                20
```